United States Patent [19]

Lange et al.

[11] Patent Number: 4,650,865

[45] Date of Patent: Mar. 17, 1987

[54] PROCESS FOR PREPARING TERTIARY ETHER AMINES

[75] Inventors: Fritz Lange, Essen; Alfred Meffert, Monheim, both of Fed. Rep. of Germany

[73] Assignee: Henkel Kommanditgesellschaft auf Aktien, Duesseldorf, Fed. Rep. of Germany

[21] Appl. No.: 827,844

[22] Filed: Feb. 7, 1986

[30] Foreign Application Priority Data

Feb. 8, 1985 [DE] Fed. Rep. of Germany ....... 3504242

[51] Int. Cl.$^4$ ..................... C07C 85/24; C07D 295/08
[52] U.S. Cl. .................................. 544/174; 544/177; 544/398; 546/236; 546/248; 548/574; 548/575; 564/347; 564/348; 564/504; 564/505; 564/508
[58] Field of Search ....................... 544/174, 177, 398; 546/236, 248; 548/574, 575; 564/347, 348, 504, 505, 508

[56] References Cited

FOREIGN PATENT DOCUMENTS 102140 11/1984 European Pat. Off. .
1087413 10/1967 United Kingdom .

OTHER PUBLICATIONS

Karrer, *Organic Chemistry*, 4th English edition, (1950), pp. 115, 430, 431, Elsevier Publishing Company, Inc.

*Primary Examiner*—Robert W. Ramsuer
*Attorney, Agent, or Firm*—Ernest G. Szoke; Henry E. Millson, Jr.

[57] ABSTRACT

The invention relates to a process for preparing tertiary ether amines corresponding to the following general formula:

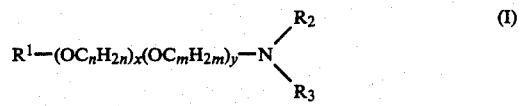

by reacting in the presence of a strong base of a tertiary amine corresponding to the following formula:

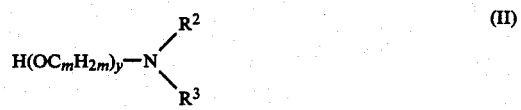

with a sulfuric acid semi-ester salt corresponding to the following formula:

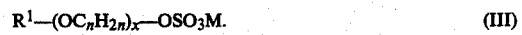

Preferably, each mole of the tertiary amine corresponding to formula (II) is reacted under substantially anhydrous conditions at a temperature of 140° to 230° C. with from about 0.2 to 3.0 moles of the sulfuric acid semi-ester salt of formula (III) in the presence of from about 1 to 1.5 moles of a strong base preferably an alkali metal hydroxide or an alkali metal alcoholate.

11 Claims, No Drawings

PROCESS FOR PREPARING TERTIARY ETHER AMINES

BACKGROUND OF THE INVENTION

1. Field of the Invention

This invention relates to a new process for producing tertiary ether amines.

2. Description of Related Art

Various processes are known for preparing tertiary ether amines, e.g., by alkylation of primary and secondary amines, for example, using alkyl, alkenyl or alkylphenyl, polyglycol ether sulfates (sulfate esters). Processes of this type are described, for example, in British Pat. No. 1,087,413 and in European Patent Application No. 102,140. However, only a limited range of tertiary ether amines can be prepared using these processes because the available secondary amines required for these processes are often not available or are difficult to obtain.

DESCRIPTION OF THE INVENTION

It now has been found surprisingly that tertiary ether amines corresponding to the general formula

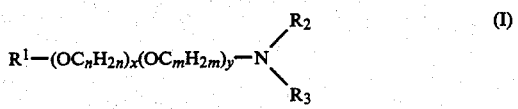

wherein $R^1$ is an alkyl or alkenyl group containing from 6 to 22 carbon atoms or an alkyl or dialkyl phenyl group containing from 6 to 16 carbon atoms in the alkyl group, n and m are integers having a value of from 2 to 4, x is a number having a value of from 0 to 20, y is a number having a value of from 1 to 10 and $R^2$ and $R^3$ independently of one another are an alkyl or alkenyl group having from 1 to 22 carbon atoms; an $H(OC_mH_{2m})_y$— group with m and y as defined above; and $R^1(OC_nH_{2n})_x(OC_mH_{2m})_y$— group with $R^1$, n, x, m and y as defined above, or $R^2$ and $R^3$ together with the nitrogen atom form a 5- or 6-membered ring which also may contain another nitrogen or oxygen atom, can be obtained by reaction of a tertiary amine corresponding to the following formula

with a sulfuric acid semi-ester salt corresponding to the following formula:

$$R^1\text{---}(OC_nH_{2n})_x\text{---}OSO_3M \qquad (III)$$

in which M is an alkali metal or alkaline earth metal. The meanings of $R^1$, $R^2$, $R^3$, m, n, x and y in formula (II) and (III) are the same as defined for formula (I).

If the tertiary amine corresponding to formula (II) has only one hydroxy group to be alkylated with the sulfuric acid semi-ester salt corresponding to formula (III), the reaction may be carried out with equi-molar quantities of the sulfuric acid semi-ester and tertiary amine (molar ratio of about 0.8:1 to 1:1). When the tertiary amine corresponding to formula (II) contains a second or third hydroxyl group and it is desired to suppress alkylation of the second or third hydroxyl group in a secondary reaction, it is preferred to use an excess of the amine, for example, of up to about 5 moles of amine per mole of the sulfuric acid semi-ester salt. With such a molar excess of the amine, multiple alkylation can be avoided. Unreacted amine can be separately recovered from the alkylation product and recycled.

However, in cases where it is desired to obtain tertiary ether amines corresponding to formula (I), in which $R^2$ and/or $R^3$ comprise groups of the formula $R^1$—$(OC_nH_{2n}O)_x(OC_mH_{2m})_y$—, each mole of a tertiary amine corresponding to formula (II), wherein for example $R^2$ and, optionally, also $R^3$ is a group of the formula $H(OC_mH_{2m})_y$—, where m and y are as defined above, should be reacted with two or three moles of the sulfuric acid semi-ester salt. In other words, for complete alkylation the ratio of the number of moles of sulfuric acid semi-ester salt to the number of moles of tertiary amine multiplied by the number of hydroxyl groups in said tertiary amine should be about 1:1.

Based on the above, in order to form tertiary ether amines corresponding to formula (I) in accordance with the present invention, each mole of a tertiary amine corresponding to formula (II) is reacted with from 0.2 to 3.0 moles of a sulfuric acid semi-ester salt corresponding to formula (III).

The reaction between the tertiary amine of formula (II) and the sulfuric acid semi-ester salt of formula (III) is carried out in the presence of at least about 1 mole of a strong base for each mole of the sulfuric acid semi-ester salt, e.g., Example 3 presented hereafter illustrates using approx. 0.9 mole of sodium hydroxide per mole of the sulfuric acid semi-ester salt. Preferably, an alkali metal hydroxide or an alkali metal alcoholate, having for example, 1 to 4 carbon atoms is used and it is particularly preferred to use a base having the same cation as the sulfuric acid semi-ester salt. The base neutralizes any hydrogen sulfates formed during the reaction between the semi-ester salt and the tertiary amine. Where an alkali metal hydroxide is used, 1 mole of water and, where an alcoholate is used, 1 mole of an alcohol is formed for each mole of sulfuric acid semi-ester salt consumed during the reaction. This water or alcohol is distilled from the reaction mixture as the reaction proceeds. It is preferred to use the strong base in a slight excess, for example, in an amount of from about 1 to 1.75 moles per mole of sulfuric acid semi-ester salt. Generally, no more than about 1.5 moles of base per mole of the semi-ester salt is needed. Based on availability and cost, sodium hydroxide and sodium methylate are the preferred bases.

There is no need to conduct the reaction in an inert solvent. Moreover, the reaction between the semi-ester and the tertiary amine should be conducted under substantially anhydrous conditions because at the reaction conditions water promotes hydrolysis of the sulfuric acid semi-ester salt.

In one particularly preferred process, a reaction mixture is prepared from an amine corresponding to formula (II), a sulfuric acid semi-ester corresponding to the following formula $$R^1\text{---}(OC_nH_{2n})_x\text{---}OSO_3H \qquad (IV)$$

and 2 to 2.5 moles of a strong base per each mole of sulfuric acid semi-ester. The mixture then is reacted under the appropriate conditions described hereafter. It is thought that the sulfuric acid semi-ester salt forms in situ and then reacts with the tertiary amine. In formula (IV), $R^1$, n and x have the same meanings as defined above in connection with formulae (I) and (III). The advantage of this procedure is that there is no need to dehydrate the sulfuric acid semi-ester salt beforehand. The water or alcohol formed through salt formation during the reaction between the tertiary amine and the sulfuric acid semi-ester salt simply is distilled from the reaction mixture as the reaction proceeds.

The reaction between the tertiary amine and the sulfuric acid semi-ester salt takes place substantially quantitatively at a temperature within the range of about 140° to 230° C., preferably at about 200° C., over a period of about 1 to 5 hours, preferably for about 2 to 3 hours. The principal competing reactions are hydrolysis of the sulfuric acid semi-ester salt, multiple alkylation where amines containing several hydroxyl groups are used and oxidative discolorization. These competing reactions may be suppressed by maintaining substantially anhydrous conditions, by the judicious selection of the molar ratio of the reactants and by working in an inert gas atmosphere, for example, under a nitrogen atmosphere.

On completion of the reaction, the reaction mixture may be purified by washing with water or, where readily water-soluble ether amines are involved, by washing with a saturated sodium chloride solution or soda solution. In this way, water-soluble secondary products, such as alkali sulfates, magnesium sulfate and unreacted amines, are removed from the desired amine product. The product then may be dried using standard methods and equipment.

Suitable tertiary amine starting materials corresponding to formula (II) for use in the present invention include, for example, triethanolamine, methyl diethanolamine, dimethyl ethanolamine, N-hydroxyethyl morpholine, dimethyl isopropanolamine, triisopropanolamine, adducts of from 2 to 20 moles of ethylene oxide, propylene oxide and/or butylene oxide with primary alkylamines of the formula $R^2$—$NH_2$ and adducts of from 1 to 10 moles of these alkylene oxides with dialkylamines of the formula $R^2$—NH—$R^3$, where $R^2$ and $R^3$ are as defined above. Adducts such as these include, for example, the adducts of ethylene oxide or propylene oxide with primary fatty amines, with dialkylamines such as dimethyl amine or diethylamine or with morpholine.

Suitable sulfuric acid semi-ester salts corresponding to general formula (III) include, for example, the lithium, sodium, potassium or magnesium salts of $C_6$-$C_{22}$ saturated and unsaturated fatty alcohol sulfates, for example, n-octyl sulfate, n-lauryl sulfate, n-cetyl sulfate, n-stearyl sulfate, oleyl sulfate, behenyl sulfate and n-erucyl sulfate. The sulfuric acid semi-ester salts of branched primary $C_6$-$C_{22}$ alcohols, for example 2-ethylhexyl sulfate, isononyl sulfate or 2-hexyl decyl sulfate, also are suitable. Other suitable sulfuric acid semi-ester salts of formula (III) can be prepared by sulfation, e.g., using sulfuric acid and the like, of the adducts of primary and secondary $C_6$-$C_{22}$ saturated and unsaturated alcohols or alkyl phenols or dialkyl phenols containing from 6 to 16 carbon atoms in the alkyl group with up to 20 moles and preferably from 1 to 20 moles of ethylene oxide, propylene oxide or butylene oxide. Ether sulfates of this type are widely used as high-foam surfactants for commercial and cosmetic applications and thus may be easily and inexpensively obtained in large quantities.

Anhydrous sulfuric acid semi-ester salts of formula (III) suitable for preparing the desired tertiary ether amines of formula (I) may be obtained, for example, by dehydration of such commercially available aqueous solutions of alkyl sulfates, alkenyl sulfates, alkyl ether sulfates or alkyl phenol polyglycol ether sulfates.

The reaction of ethylene oxide, propylene oxide and/or butylene oxide with primary and secondary alcohols and with alkyl phenols can be carried out in the presence of basic catalysts, for example sodium methylate, sodium hydroxide or calcium acetate, or can be conducted in the presence of acidic catalysts, such as boron trifluoride, for example, using conditions well known to those skilled in the art. Homolog mixtures of the alkyl and alkylphenyl polyoxyalkylene adducts are obtained in which the average degree of alkoxylation (identified by x in the above formula) corresponds to the molar ratio of the alkylene oxide to the alcohol or alkyl phenol.

The reaction of the alkylene oxides with primary and secondary amines discussed previously also can be carried out in the presence of basic catalysts, and similarly yields amines having a range of polyalkylene glycol ether chain lengths representing a homolog mixture wherein the average degree of alkoxylation corresponds to the original molar ratio of the alkylene oxide to the amine. In general, in formula (I), (II) and (III) above, the numbers x for values of from 0 to 20 and y for values of from 1 to 10 thus represent the average degree of alkoxylation of the homolog mixture corresponding to the molar proportion of the alkylene oxide used.

The water solubility and other properties important for particular uses of the ether amines produced in accordance with the invention may be controlled within a wide range through the type and number of oxyalkylene groups in the sulfuric acid semi-ester salt (n and x in formula (III)) on the one hand and in the tertiary amine (m and y in formula (II)) on the other hand. The process of the present invention makes it possible to produce ether amines which can be obtained only with considerable difficulty, if at all, by previously known processes.

The ether amines produced in accordance with the present invention are suitable for numerous applications, for example as surfactants and as starting materials for the production of surface-active derivatives, such as for example, amine oxides and quaternary ammonium compounds.

The following Examples are intended to illustrate the present invention without limiting its scope in any way, which is defined in the appended claims.

EXAMPLES

Example 1: Preparation of n-Octyloxyethyl dihydroxyethyl amine 40.3 grams of a 30% (by weight) solution of sodium methylate in methanol (0.224 mole) were added to 100 grams of triethanolamine (0.67 mole), after which the methanol was distilled off by heating to 110° C. 51.6 grams of n-octyl sulfate, Na salt (0.22 mole) were stirred at 20° C. into the solution obtained and the reaction mixture was heated for 4 hours to 200° C. After cooling to 20° C., approx. 160 ml of water were added. Two liquid phases formed. The upper phase was separated off, washed twice with water and dried under a vacuum in a rotary vaporator with gentle heating to approx. 80° C. A brown oily liquid (52 grams) having an amine number of 214 was obtained (the amine number indicates the number of mg of KOH equivalent to 1 gram of the substance).

When the reaction was carried out under a nitrogen atmosphere, the ether amine obtained was pale yellow in color.

Example 2: Lauryl/myristyl poly-(3.6)-oxyethyl dihydroxyethyl amine 300 grams (0.456 mole) of $C_{12}$–$C_{14}$ (1:1) fatty alcohol-(3.6-EO)-sulfate, Na salt (sulfuric acid semi-ester salt of the adduct of 3.6 moles of ethylene oxide per each mole of a fatty alcohol mixture of 50% by weight of lauryl alcohol and 50% by weight myristyl alcohol—supplied as a 70% by weight aqueous solution) were combined with 67.9 grams (0.456 mole) of triethanolamine and substantially dehydrated in a water jet vacuum at 100° C. in a rotary evaporator. After purging the reaction vessel with nitrogen, 18.3 grams of sodium hydroxide (0.456 mole) were added, followed by repurging with nitrogen. Then, the reaction mixture was heated for 3 hours to 200° C. After cooling to 20° C., the mixture was washed repeatedly with a saturated sodium chloride solution and dried with heating to 100° C. under a vacuum in a rotary evaporator. Sodium chloride precipitated from the product was filtered off. A yellow oil having an amine number of 95 was obtained in a quantity of 185.0 grams.

Example 3: Lauryl/myristyl poly-(3.6)-oxyethyl hydroxyethyl methylamine 230 grams (0.35 mole) of $C_{12}$–$C_{14}$ (1:1) fatty alcohol-(3.6-EO)-sulfate, Na salt (70% aqueous solution used in Example 2), 54.3 grams (0.456 mole) of N-methyl diethanolamine and 12.8 grams of sodium hydroxide (0.32 mole) were reacted and the product purified in the same way as in Example 2. A pale yellow oil having an amine number of 104 was obtained in a quantity of 130 grams.

Example 4: Lauryl/myristyl poly-(2)-oxyethyl dihydroxyethyl amine 968 grams (1.67 moles) of $C_{12}$–$C_{14}$ (7:3) fatty alcohol-2-EO-sulfate, Na salt (65.8% aqueous solution), 300.7 grams (2.018 moles) of triethanolamine and 80.7 grams (2.018 moles) of sodium hydroxide were reacted and the product purified in the same way as in Example 2. A yellow-brown oil having an amine number of 111.4 was obtained in a quantity of 565 grams.

Example 5: n-Octyloxyethyl hydroxyethyl methyl amine 318 grams (1.377 moles) of n-octyl sulfate, Na salt, 491.5 grams (4.130 moles) of N-methyl diethanolamine and 55.1 grams (1.377 moles) of sodium hydroxide were heated with stirring for 3 hours under a nitrogen atmosphere to 200° C. After cooling to 80° C., the mixture was washed four times with saturated sodium chloride solution and then dried at 80° C. under a vacuum in a rotary evaporator. Sodium chloride precipitated from the product was filtered. A red-brown liquid having an amine number of 238 was obtained in a quantity of 254 grams.

Example 6: Cetyl-/stearyl-oxyethyl dihydroxyethyl amine 467 grams (0.69 mole) of cetyl-/steryl (30:70)-sulfate, Na salt (53.5% aqueous paste), 149.2 grams (1.0 mole) of triethanolamine and 48.0 grams (1.2 moles) of sodium hydroxide were reacted and the product purified in the same way as in Example 2. A dark oil having an amine number of 129.6 was obtained in a quantity of 238 grams.

Example 7: Di-(cetyl/stearyl-oxyethyl)-hydroxyethyl amine 338.7 grams (0.5 mole) of cetyl-/stearyl (30:70)-sulfate, Na salt (53.5% aqueous paste), 201.1 grams (0.5 mole) of cetyl-/stearyl-oxyethyl dihydroxyethyl amine (corresponding to the product of Example 6) and 21.0 grams (0.53 mole) of sodium hydroxide were reacted and the product purified in the same way as in Example 2. A dark brown oil having an amine number of 70.8 was obtained in a quantity of 241 grams.

Example 8: Lauryl/myristyl-poly-(3)-oxyethyl dihydroxyethyl amine 404 grams (1 mole) of $C_{12}$–$C_{14}$ fatty alcohol (70:30)-(3-EO)-sulfuric acid semi-ester were slowly added in a dropwise manner at 40° C. to 179 grams (1.2 moles) of triethanolamine. 84 grams (2.1 moles) of sodium hydroxide then were added and the reaction mixture slowly heated with stirring. Vigorous foaming started at about 145° C. and water was distilled off from the reaction mixture under a slight vacuum. The reaction mixture then was maintained at 180° C. for 1.5 hours and, after cooling to 20° C., was purified in the same way as in Example 2.

A yellow oil having an amine number of 86.7 was obtained in a quantity of 377 grams.

Example 9: Lauryloxyethyl $C_8$–$C_{18}$-cocosalkyl hydroxyethyl amine 48 grams (1.2 moles) of sodium hydroxide and 288.4 grams (1 mole) of n-lauryl sulfate, Na salt were added to 312 grams (1.1 moles) of $C_8$–$C_{18}$ cocosalkyl dihydroxyethyl amine (adduct of 2 moles of ethylene oxide with a $C_8$–$C_{18}$ coconut oil fatty amine) and the mixture was slowly heated in a nitrogen atmosphere. Water began to distill at about 140° C. The reaction mixture was maintained at 200° C. for a total of 2 hours. After cooling to 20° C., the reaction mixture was purified in the same way as in Example 2. An oily liquid having an amine number of 137 and a hydroxy number of 182 was obtained in a quantity of 293 grams.

Example 10: Lauryloxyethyl hydroxyethyl methylamine 40 grams (1 mole) of sodium hydroxide and 288.4 grams (1 mole) of n-lauryl sulfate, Na salt were added to 143.1 grams (1.2 moles) of N-methyl diethanolamine and the mixture was reacted and purified in the same manner as in Example 9.

A yellow oil having an amine number of 171 and a hydroxyl number of 153 was obtained in a quantity of 156 grams.

Distillation of the crude product gave 95 grams (approx. 61% by weight) of a fraction which boiled at 125°–160° C./0.001 Torr and had an amine number of 188.

Example 11: Di-(lauryloxyethyl)-methylamine 43.1 grams (0.145 mole) of the pure fraction obtained in accordance with Example 10 (i.e, the product having an amine number of 188) were reacted with 6.5 grams (0.15 mole) of NaOH and 43.3 grams (0.15 mole) of lauryl sulfate, Na salt using the procedure of Example 9.

Purification of the product, again in accordance with the procedure of Example 9, gave 34 grams of a yellow oil having an amine number of 125.

Example 12: Lauryloxyethyl dihydroxyethyl amine and di-(lauryloxyethyl)-hydroxyethyl amine 149.2 grams (1 mole) of triethanolamine, 48 grams (1.2 moles) of sodium hydroxide and 288.4 grams (1 mole) of lauryl sulfate Na salt were slowly heated under a nitrogen atmosphere in a flask provided with a stirrer and equipped with a dephlegmator. Water began to distill at about 140° C. The reaction mixture was further heated to 200° C. with removal of water and volatile secondary products and was maintained at that temperature for 2 hours. Purification of the product using the procedure of Example 9 gave 218 grams of a crude product having an amine number of 148.

Distillation of the crude product gave 138 grams of a fraction which boiled at 175° C./0.001 Torr and had an amine number of 176. This product was identified as lauryloxyethyl dihydroxyethyl amine (theoretical amine number 176.3).

67 grams of a second fraction which boiled at 235° C./0.001 Torr and had an amine number of 118 also were obtained. This product corresponds to di-(lauryloxyethyl)-hydroxyethyl amine (theoretical amine number 115.7).

In addition to these first and second fractions 10 grams of first runnings and 3 grams of residue also were obtained.

Example 13: Tris-(lauryloxyethyl)-amine 20 grams (0.042 mole) of di-(lauryloxyethyl)-hydroxyethyl amine (the second fraction recovered in Example 12) were reacted with 2.0 grams (0.05 mole) of sodium hydroxide and 12.1 grams (0.042 mole) of lauryl sulfate, Na salt using the procedure of Example 12. Purification of the product again using the procedure of Example 12, gave 32 grams of a yellow oily product having an amine number of 85.6.

Example 14: Lauryloxyethyl diethylamine 140.6 grams (1.2 moles) of diethyl ethanolamine, 48 grams (1.2 moles) of sodium hydroxide and 288.4 grams (1 mole) of lauryl sulfate, Na salt were reacted under a nitrogen atmosphere using the procedure of Example 9. Approx. 20 grams of the diethyl ethanolamine evaporated from the reaction with water during the reaction and was immediately replaced. After a reaction time of 2 hours at 190° C., followed by cooling to 20° C., the reaction mixture was purified using the procedure of Example 2. 168 grams of an oily liquid having an amine number of 151 were obtained.

Example 15: N-lauryloxyethyl morpholine 157.5 grams (1.2 moles) of N-(2-hydroxyethyl)morpholine, 48 grams (1.2 moles) of sodium hydroxide and 288.4 grams (1 mole) of lauryl sulfate, Na salt were reacted under a nitrogen atmosphere using the procedure of Example 9. Purification of the product, again using the procedure of Example 9, gave 246 grams of crude product from which 59 grams of an oily liquid having an amine number of 154 was isolated after repeated washing with sodium chloride solution.

Although certain embodiments of the present invention have been described in detail, it will be appreciated that other embodiments are contemplated along with modification of the disclosed features, as being within the scope of the invention, which is defined in the appended claims.

We claim:

1. A process for preparing tertiary ether amines corresponding to the following general formula $$R^1-(OC_nH_{2n})_x(OC_mH_{2m})_y-N\begin{matrix}R_2\\R_3\end{matrix} \qquad (I)$$

wherein $R^1$ is an alkyl or alkenyl group containing from 6 to 22 carbon atoms or an alkyl or dialkyl phenyl group containing from 6 to 16 carbon atoms in the alkyl group, n and m are integers having a value of from 2 to 4, x is a number having a value of from 0 to 20, y is a number having a value of from 1 to 10 and $R^2$ and $R^3$ independently of one another are an alkyl or alkenyl group having from 1 to 22 carbon atoms; an $H(OC_mH_{2m})_y-$ group, an $R^1(OC_nH_{2n})_x-(OC_mH_{2m})_y-$ group, or together with the nitrogen atom, form a 5- or 6-membered ring which may contain another nitrogen or oxygen atom, comprising reacting in the presence of a strong base a tertiary amine corresponding to the following formula:

$$H(OC_mH_{2m})_y-N\begin{matrix}R^2\\R^3\end{matrix} \qquad (II)$$

with a sulfuric acid semi-ester salt corresponding to the following formula:

$$R^1-(OC_nH_{2n})_x-OSO_3M \qquad (III)$$

wherein M is an alkali metal or alkaline earth metal ion, and $R^1$, $R^2$, $R^3$, m, n, x and y are as defined above.

2. The process of claim 1, wherein the tertiary amine corresponding to formula (II) is reacted at a temperature of about 140° to 230° C. under substantially anhydrous conditions with from about 0.2 to 3.0 moles of the sulfuric acid semi-ester salt of formula (III) per mole of said tertiary amine in the presence of from at least about 1 to 1.75 moles of an alkali metal hydroxide or alkali metal alcoholate per mole of said tertiary amine.

3. The process of claim 1, wherein a reaction mixture is prepared initially from the tertiary amine of formula (II), a sulfuric acid semi-ester corresponding to the following formula:

$$R^1-(OC_nH_{2n})_x-OSO_3H \qquad (IV)$$

wherein $R^1$, n and x are as defined above, and 2 to 2.5 moles of a strong base per mole of said sulfuric acid semi-ester prior to reacting said tertiary amine and said sulfuric acid semi-ester salt.

4. A process for preparing tertiary ether amines corresponding to the following general formula

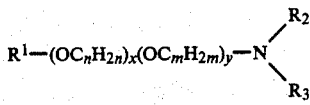

wherein
- $R^1$ is an alkyl or alkenyl group containing from 6 to 22 carbon atoms or an alkyl or dialkyl phenyl group containing from 6 to 16 carbon atoms in the alkyl group,
- n and m are integers having a value of from 2 to 4,
- x is a number having a value of from 0 to 20,
- y is a number having a value of from 1 to 10 and
- $R^2$ and $R^3$ independently of one another are an alkyl or alkenyl group having from 1 to 22 carbon atoms; an $H(OC_mH_{2m})_y-$ group, an $R^1(OC_nH_{2n})_x-(OC_mH_{2m})_y-$ group, or together with the nitrogen atom, form a 5- or 6-membered ring which may contain another nitrogen or oxygen atom, comprising reacting in the presence of a strong base a tertiary amine corresponding to the following formula:

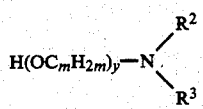

with a sulfuric acid semi-ester corresponding to the following formula:

$$R^1-(OC_nH_{2n})_x-OSO_3H \qquad (IV)$$

wherein $R^1$, $R^2$, $R^3$, m, n, x and y are as defined above.

5. The process of claim 4, wherein the tertiary amine corresponding to formula (II) is reacted at a temperature of about 140° to 230° C. under substantially anhydrous conditions with from about 0.2 to 3.0 moles of the sulfuric acid semi-ester of formula (IV) per mole of said tertiary amine in the presence of from at least about 2 to 2.5 moles of an alkali metal hydroxide or alkali metal alcoholate per mole of said tertiary amine.

6. The process of claim 1 wherein said tertiary amine is selected from the group consisting of triethanolamine, methyl diethanolamine, dimethyl ethanolamine, N-hydroxyethyl morpholine, dimethyl isopropanolamine, triisopropanolamine, adducts of from 2 to 20 moles of ethylene oxide, propylene oxide and/or butylene oxide with primary alkylamines of the formula $R^2-NH_2$ and adducts of from 1 to 10 moles of these alkylene oxides with dialkylamines of the formula $R^2-NH-R^3$, where $R^2$ and $R^3$ are as defined above.

7. The process of claim 6 wherein said sulfuric acid semi-ester salt is selected from the group consisting of the lithium, sodium, potassium or magnesium salts of n-octyl sulfate, n-lauryl sulfate, n-cetyl sulfate, n-stearyl sulfate, oleyl sulfate, behenyl sulfate, n-erucyl sulfate, 2-ethylhexyl sulfate, isononyl sulfate, 2-hexyl decyl sulfate and sulfuric acid sulfation products based on adducts of primary and secondary $C_6-C_{22}$ saturated and unsaturated alcohols or alkyl phenol or dialkyl phenols containing from 6 to 16 carbon atoms in the alkyl group with up to 20 moles of ethylene oxide, propylene oxide or butylene oxide.

8. The process of claim 2 wherein said alkali metal hydroxide is sodium hydroxide.

9. The process of claim 5 wherein said alkali metal hydroxide is sodium hydroxide.

10. The process of claim 4 wherein said tertiary amine is selected from the group consisting of triethanolamine, methyl diethanolamine, dimethyl ethanolamine, N-hydroxyethyl morpholine, dimethyl isopropanolamine, triisopropanolamine, adducts of from 2 to 20 moles of ethylene oxide, propylene oxide and/or butylene oxide with primary alkylamines of the formula $R^2-NH_2$ and adducts of from 1 to 10 moles of these alkylene oxides and dialkylamines of the formula $R^2-NH-R^3$, where $R^2$ and $R^3$ are as defined above.

11. The process of claim 10 wherein said sulfuric acid semi-ester is selected from the group consisting of n-octyl sulfate, n-lauryl sulfate, n-cetyl sulfate, n-stearyl sulfate, oleyl sulfate, behenyl sulfate, n-erucyl sulfate, 2-ethylhexyl sulfate, isononyl sulfate, 2-hexyl decyl sulfate and sulfuric acid sulfation products based on adducts of primary and secondary $C_6-C_{22}$ saturated and unsaturated alcohols or alkyl phenol or dialkyl phenols containing from 6 to 16 carbon atoms in the alkyl group with up to 20 moles of ethylene oxide, propylene oxide or butylene oxide.

* * * * *